US008655597B2

(12) United States Patent
Oka et al.

(10) Patent No.: US 8,655,597 B2
(45) Date of Patent: Feb. 18, 2014

(54) SCORING SYSTEM FOR THE PREDICTION OF CANCER RECURRENCE

(75) Inventors: Masaaki Oka, Ube (JP); Yoshihiko Hamamoto, Ube (JP); Hisafumi Okabe, Yokohama (JP)

(73) Assignee: F. Hoffmann-La Roche AG, Basel (CH)

( * ) Notice: Subject to any disclaimer, the term of this patent is extended or adjusted under 35 U.S.C. 154(b) by 647 days.

(21) Appl. No.: 12/759,263

(22) Filed: Apr. 13, 2010

(65) Prior Publication Data
US 2012/0065892 A1 Mar. 15, 2012

Related U.S. Application Data

(62) Division of application No. 10/484,664, filed as application No. PCT/JP01/06330 on Jul. 23, 2001, now Pat. No. 7,747,389.

(51) Int. Cl.
G06F 7/00 (2006.01)
(52) U.S. Cl.
USPC ................ 702/19; 702/20; 703/11; 707/700; 435/6.1
(58) Field of Classification Search
None
See application file for complete search history.

(56) References Cited

U.S. PATENT DOCUMENTS

| | | | |
|---|---|---|---|
| 5,800,347 | A | 9/1998 | Skates et al. |
| 5,862,304 | A | 1/1999 | Ravdin et al. |
| 6,025,128 | A | 2/2000 | Veltri et al. |
| 6,030,341 | A | 2/2000 | Skates et al. |
| 6,128,608 | A | 10/2000 | Barnhill |
| 6,647,341 | B1 | 11/2003 | Golub et al. |
| 6,728,642 | B2 | 4/2004 | Bloch et al. |
| 7,243,112 | B2 | 7/2007 | Qu et al. |
| 7,747,389 | B2 | 6/2010 | Oka et al. |
| 2001/0036631 | A1 | 11/2001 | McGraft et al. |
| 2002/0192686 | A1 | 12/2002 | Adorjan et al. |
| 2007/0292423 | A1 | 12/2007 | Oka et al. |

FOREIGN PATENT DOCUMENTS

| | | |
|---|---|---|
| AU | 7980691 A | 12/1991 |
| AU | 7830598 A | 12/1998 |
| AU | 5897600 A | 1/2001 |
| AU | 7701100 A | 4/2001 |
| AU | 1465801 A | 5/2001 |
| AU | 1806701 A | 6/2001 |
| CA | 2229427 A1 | 3/1997 |
| DE | 19840671 A1 | 3/2000 |
| EP | 0957749 A2 | 11/1999 |
| EP | 1043676 A2 | 10/2000 |
| JP | 2001-017171 A | 1/2001 |
| WO | WO 91/18364 A1 | 11/1991 |
| WO | WO 97/09925 A2 | 3/1997 |
| WO | WO 97/09925 A3 | 3/1997 |
| WO | WO 98/56953 A1 | 12/1998 |
| WO | WO 01/00083 A1 | 1/2001 |
| WO | WO 01/18542 A2 | 3/2001 |
| WO | WO 01/18542 A3 | 3/2001 |
| WO | WO 01/33228 A2 | 5/2001 |
| WO | WO 01/33228 A3 | 5/2001 |
| WO | WO 01/40517 A2 | 6/2001 |
| WO | WO 01/40517 A3 | 6/2001 |
| WO | WO 03/010337 A1 | 2/2003 |
| WO | WO 2004/090163 A1 | 10/2004 |

OTHER PUBLICATIONS

Bromberg, J.F., "Activation of STAT Proteins and Growth Control", *BioEssays*, vol. 23, pp. 161-169, 2001.
Burnette, W.N., "Western Blotting": Electrophoretic Transfer of Proteins from Sodium Dodecyl Sulfate-Polyacrylamide Gels to Unmodified Nitrocellulose and Radiographic Detection with Antibody and Radioiodinated Protein A, *Analytical Biochemistry*, vol. 112, pp. 195-203, 1981.
Bustin, S.A., "Absolute Quantification of mRNA Using Real-Time Reverse Transcription Polymerase Chain Reaction Assays", *Journal of Molecular Endocrinology*, vol. 25, pp. 169-193, 2000.
Carreira, C.M., et al., "LYVE-1 Is Not Restricted to the Lymph Vessels: Expression in Normal Liver Blood Sinusoids and Down-Regulation in Human Liver Cancer and Cirrhosis", *Cancer Research*, vol. 61, pp. 8079-8084, 2001.
Colombo, M., "Hepatitis C Virus and Hepatocellular Carcinoma", *Seminars in Liver Disease*, vol. 19, No. 3, pp. 263-269, 1999.
Covell, D.G., et al., "Molecular Classification of Cancer: Unsupervised Self-Organizing Map Analysis of Gene Expression Microarray Data," *Molecular Cancer Therapeutics*, 2:317-332 (2003).
Delpuech, O., et al., "Identification, Using cDNA Macroarray Analysis, of Distinct Gene Expression Profiles Associated with Pathological and Virological Features of Hepatocellular Carcinoma," *Oncogene*, 21(18):2926-2937 (2002).
DeRisi, J., et al., "Use of a cDNA microarray to analyse gene expression patterns in human cancer", *Nature Genetics*, vol. 14, downloaded from http://www.nature.com/naturegenetics, pp. 457-460, 1996.
Edmondson, H.A. and Steiner, P.E., "Primary Carcinoma of the Liver", *Cancer*, vol. 7, No. 3, pp. 462-503, 1954.
Engvall, E., and Perlmann, P., "Enzyme-linked Immunosorbent Assay (ELISA) Quantitative Assay of Immunoglobulin G",*Immunochemistry*, vol. 8, pp. 871-874, 1971.

(Continued)

*Primary Examiner* — Mary Zeman
(74) *Attorney, Agent, or Firm* — Hamilton, Brook, Smith & Reynolds, P.C.

(57) ABSTRACT

The present invention relates to a scoring system for the prediction of cancer recurrence by selecting genes and/or proteins whose expression patterns associated with recurrence of cancer, and generating formulae with the selected genes and/or proteins for the prediction of cancer recurrence. The present invention relates to a kit for determining the likelihood of recurrence of cancer, comprising DNA chip, oligonucleotide chip, protein chip, peptides, antibodies, probes and primers that are necessary for effecting DNA microarrays, oligonucleotide microarrays, protein arrays, northern blotting, in situ hybridization, RNase protection assays, western blotting, ELISA assays, reverse transcription polymerase-chain reaction to examine the expression of at least 2, 4, 6, 10, 12 or more genes and/or proteins, that are indicative of cancer recurrence.

20 Claims, 5 Drawing Sheets

(56) References Cited

OTHER PUBLICATIONS

Giannelli, G., et al., "Transforming Growth Factor-β1 Triggers Hepatocellular Carcinoma Invasiveness Via α3β1 Integrin," *American Journal of Pathology*, 161(1): 183-193 (2002).

Hod, Y., "A Simplified Ribonuclease Protection Assay", *BioFeedback*, vol. 13, No. 6, pp. 852-855, 1992.

Hung, W-C. and Chuang, L-Y., "Sodium Butyrate Enhances STAT 1 Expression in PLC/PRF/5 Hepatoma Cells and Augments Their Responsiveness to Interferon-α", *British Journal of Cancer*, vol. 80, pp. 705-710, 1999.

Iizuka, N., et al., "Comparison of Gene Expression Profiles Between Hepatitis B Virus- and Hepatitis C Virus-infected Hepatocellular Carcinoma by Oligonucleotide Microarray Data on the Basis of a Supervised Learning Method," *Cancer Research*, 62(14):3939-3944 (2002).

Iizuka, N., et al., "Oligonucleotide Microarray for Prediction of Early Intrahepatic Recurrence of Hepatocellular Carcinoma After Curative Resection," *Lancet*, 361(9361):923-929 (2003).

Kojiro, M., "Pathological Evolution of Early Hepatocellular Carcinoma", *Oncology*, vol. 62, pp. 43-47, 2002.

Lau, W., et al., "Differential Gene Expression of Hepatocellular Carcinoma Using cDNA Microarray Analysis", *Oncology Research*, vol. 12, pp. 59-69, 2000.

Leto, G., et al., "Cathepsin D Serum Mass Concentrations in Patients with Hepatocellular Carcinoma and/or Liver Cirrhosis", *Eur J. Clin. Chem. Clin. Biochem*, vol. 34, No. 7, pp. 525-598, 1996.

Lipshutz, R.J., et al., "High density synthetic oligonucleotide arrays", *Nature Genetics Supplement*, vol. 21, pp. 20-24, 1999.

Luo, J., et al., "Human Prostate Cancer and Benign Prostatic Hyperplasia: Molecular Dissection by Gene Expression Profiling", *Cancer Research*, vol. 61, pp. 4683-4688, 2001.

Merchant M. and Weinberger, S.R., "Recent advancements in surface-enhanced laser desorption/ionization-time of flight-mass spectrometry", *Electrophoresis*, vol. 21, pp. 1164-1167, 2000.

Midorikawa, Y., et al., "Identification of Genes Associated with Dedifferentiation of Hepatocellular Carcinoma with Expression Profiling Analysis," *Jpn. J. Cancer Res.*, 93(6): 636-643 (2002).

Murakami, K., et al., "Involvement of insulin-like growth factor binding protein-3 in the retinoic acid receptor-α-mediated inhibition of hepatocellular carcinoma cell proliferation", *Cancer Letters*, vol. 151, pp. 63-70, 2000.

Nagata, K., et al., "Expression of Hepatocyte Growth Factor Activator and Hepatocyte Growth Factor Activator Inhibitor Type 1 in Human Hepatocellular Carcinoma", *Biochemical and Biophysical Research Communications*, vol. 289, 205-211, 2001.

Ohannesian, D.W., et al., "Carcinoembryonic Antigen and Other Glycoconjugates Act as Ligands for Galectin-3 in Human Colon Carcinoma Cells1", *Cancer Research*, vol. 55, pp. 2191-2199, 1995.

Okabe, H., et al., "Genome-wide Analysis of Gene Expression in Human Hepatocellular carcinomas Using cDNA Microarray: Identification of Genes Involved in Viral Carcinogenesis and Tumor Progression", *Cancer Research*, vol. 61, downloaded from http://www.microarrays.org/software, pp. 2129-2137, 2001.

Okuda, K., "Hepatocellular carcinoma", *Journal of Hepatology*, vol. 32, pp. 225-237, 2000.

Parker, R.M.C. and Barnes, N.M., "mRNA: Detection by In Situ and Northern Hybridization", *Methods in Molecular Biology*, vol. 106, pp. 247-283.

Paweletz, C.P., et al., "Rapid Protein Display Profiling of Cancer Progression Directly From Human Tissue Using a Protein Biochip", *Drug Development Research*, vol. 49 pp. 34-42, 2000.

Radaeva, S., et al., "Interferon-α Activates Multiple STAT Signals and Down-regulates c-Met in Primary Human Hepatocytes", *Gastroenterology*, vol. 122, No. 4, pp. 1020-1034, 2002.

Saccomanno, C.F., et al., "A Faster Ribonuclease Protection Assay", *BioTechniques* 13(6):847-849, 1992.

Schafer, D.F. and Sorrell, M.F., "Hepatocellular carcinoma", *The Lancet*, vol. 353, pp. 1253-1257, 1999.

Schena, M., et al., "Quantitative Monitoring of Gene Expression Patterns with a Complementary DNA Microarray", *Science*, vol. 270, pp. 467-470, 1995.

Shirota, Y., et al., "Identification of Differentially Expressed Genes in Hepatocellular Carcinoma With cDNA Microarrays," *Hepatology*,33(4):832-840 (2001).

Shou, J., et al., "Expression profiling of a human cell line model of prostatic cancer reveals a direct involvement of interferon signaling in prostate tumor progression", *Proc. Natl. Acad. Sci. USA*, vol. 99, No. 5, pp. 2830-2835, 2002.

Spagnoli, A., et al., "Identification of STAT-1 as a Molecular Target of IGFBP-3 in the Process of Chondrogenesis", *The Journal of Biological Chemistry*, 277(21):18860-18867, 2002.

Sultan, M., et al., "Binary Tree-Structured Vector Quantization Approach to Clustering and Visualizing Microarray Data", *Bioinformatics* 18: S111-S119, 2002.

Tackels-Horne, D., et al., "Identification of Differentially Expressed Genes in Hepatocellular Carcinoma and Metastatic Liver Tumors by Oligonucleotide Expression Profiling", *Cancer*, 92(2):395-405, 2001.

Tamayo, Pablo, et al., "Interpreting patterns of gene expression with self-organizing maps: Methods and application to hematopoietic differentiation", *Proc. Natl. Acad. Sci. USA*, vol. 96, Genetics, pp. 2907-2912, 1999.

Tang, Z., "Hepatocellular Carcinoma-Cause, Treatment and Metastasis", *World J Gastroenterol* 7(4): 445-454 (2001).

Tofilon, Philip J., et al., "Enhancement of in vitro Chemotherapeutic Activity by Dimethylsulfoxide", *Clin. Expl. Metastasis*, vol. 3, No. 2, pp. 141-150, 1985.

Törönen, P., et al., "Analysis of gene expression data using self-organizing maps," *FEBS Letters*, 451:142-146 (1999).

Towbin, H., et al., "Electrophoretic transfer of proteins from polyacrylamide gels to nitrocellulose sheets: Procedure and some applications", *Proc. Nati. Acad. Sci. USA*, vol. 76, No. 9, pp. 4350-4354, 1979.

Weis, J. H., et al., "Detection of rare mRNAs via quantitative RT-PCR", *Technical Tips*, vol. 8, No. 8, pp. 263-264, 1992.

Xu, L., et al., "Expression Profiling Suggested a Regulatory Role of Liver-enriched Transcription Factors in Human Hepatocellular Carcinoma", *Cancer Research*, vol. 61, pp. 3176-3181, 2001.

Xu, X., et al., "Insight into hepatocellular carcinogenesis at transcriptome level by comparing gene expression profiles of hepatocellular carcinoma with those of corresponding noncancerous liver", *Proc. Natl. Acad. Sci. USA*, vol. 98, No. 26, pp. 15089-15094, 2001.

Yoshii, J., et al., "The Copper-Chelating Agent, Trientine, Suppresses Tumor Development and Angiogenesis in the Murine Hepatocellular Carcinoma Cells", *Int. J. Cancer*, vol. 94, pp. 768-773, 2001.

Cho, J., et al., "Gene Selection and Classification From Microarray Data Using Kernel Machine", *FEBS Letters* 571:93-98 (2004).

Iizuka, N., et al., "Prediction of Cancer Outcome With Microarrays," The Lancet 365:1683-1684 (2005).

Iizuka, N., et al., "Predicting Individual Outcomes in Hepatocellular Carcinoma," The Lancet 364:1837-1839 (2004).

Iizuka, N., et al., "Translational Microarray Systems for Outcome Prediction of Hepatocellular Carcinoma," Cancer Sci 99(4):659-665 (2008).

Miyamoto, T., et al., "Comparison of microarray-based predictive systems for early recurrence of cancer," Pattern Recognition, 2004, ICPR 2004, Proceedings of the 17th International Conference, vol. 2, pp. 247-350.

Jain, A.K., et al., "Statistical Pattern Recognition: A Review," *IEEE Transactions on Pattern Analysis and Machine Intelligence*, 22(1):4-37 (2000).

Oka, M., et al., "Prediction of early intrahepatic recurrence in hepatocellular carcinoma after curative resection by oligonucleotide microarray," *The 60th Annual Meeting of Japanese Cancer Society*, Sep. 26, 2001, Abstract S4-6.

Duda, R.O., et al., *Pattern Classification*, Second Edition, John Wiley and Sons, Inc., New York: pp. 117, 2000.

Aburatani, H., "Clinical Application of DNA Chip Technology", *Rinshokagaku*, 30:7-14 (2001). Translated Into English From Japanese Document.

(56) References Cited

OTHER PUBLICATIONS

Alizadeh, A.A., et al., "Distinct Types of Diffuse Large B-cell Lymphoma Identified by Gene Expression Profiling", *Nature*, 403:503-511 (2000).

Anzai, H., et al., "Expression of Metastasis-related Genes in Surgical Specimens of Human Gastric Cancer can Predict Disease Recurrence", *European J. of Cancer*, 34(4):558-565 (1998).

Ben-Dor, A., et al., "Tissue Classification with Gene Expression Profiles", *J. Comput. Biol.*, 7(3/4):559-583 (2000).

Golub, T.R., et al., "Molecular Classification of Cancer: Class Discovery and Class Prediction by Gene Expression Monitoring", *Science*, 286:531-537 (1999).

Mauri, F.A., et al., "Prognostic Value of Estrogen Receptor Status can be Improved by Combined Evaluation of p53, Bc12 and PgR Expression: An Immunohistochemical Study on Breast Carcinoma with Long-term Follow-up", *Int. J. Oncol.*, 15:1137-1147 (1999).

Xiong, Momaio et al., "Computational Methods for Gene Expression-Based Tumor Classification", *BioTechniques* 29: 1264-1270 (Dec. 2000).

Cho, et al., FEBS, 571:93-98 (2004).

Fig. 1

| |
|---|
| Step 1. Divide 33 available samples into 30 training samples and 3 test samples by the cross-validation method. |
| Step 2. Compute the Fisher criterion using 30 training samples. |
| Step 3. Select superior 50 genes for discrimination between Groups A and B based on both the Fisher criterion and fold-change. |
| Step 4. Select the candidate gene subsets out of 50 genes by the exhaustive search with the leave-one-out method. |
| Step 5. Repeat Steps 1-4 independently (10 times). |
| Step 6. Select the optimal gene subset which most frequently appears in 10 trials. |
| Step 7. Determine the optimal number of the genes according to the criterion J computed with the 10 different sets of the training samples. |
| ---------------------------------------------------------------- |
| Step 8. Design the scoring system using 30 training samples selected in Step 1. |
| Step 9. Discriminate 3 test samples selected in Step 1 by the scoring system designed in Step 8. |
| Step 10. Repeat Steps 8 and 9 independently 10 times with 10 different sets of the training and test samples. |

SEQUENCE LISTING

<160> NUMBER OF SEQ ID NOS: 1

<210> SEQ ID NO 1
<211> LENGTH: 20
<212> TYPE: DNA
<213> ORGANISM: Artificial Sequence
<220> FEATURE:
<223> OTHER INFORMATION: oligonucleotide

<400> SEQUENCE: 1
ctgaacggta gcatcttgac                                        20

SCORING SYSTEM FOR THE PREDICTION OF CANCER RECURRENCE

RELATED APPLICATIONS

This application is a divisional of U.S. application Ser. No. 10/484,664, filed Jun. 22, 2004, now U.S. Pat. No. 7,747,389 which is the U.S. National Stage of International Application No. PCT/JP01/06330, filed on Jul. 23, 2001, designating the United States, published in English.

The entire teachings of the above applications are incorporated herein by reference.

BACKGROUND OF THE INVENTION

Cancer is one of the major causatives of death in the world. The overall prevalence rate of cancer is about 1% of the population and yearly incidence rate is about 0.5%. About one out of ten patients discharged from hospitals have cancer as their primary diagnosis. The main existing treatment modalities are surgical resection, radiotherapy, chemotherapy, and biological therapy including hormonal therapy. Furthermore, newly developed biotechnologies have been offering new treatment modalities, such as gene therapy. Nevertheless, cancer is dreaded disease because in most cases there is no really effective treatment available. One of the major difficulties of cancer treatment is the ability of cancer cells to become resistant to drugs and to spread to other sites of tissues, where they can generate new tumors, which often results in recurrence. If a cancer recurrence is predictable before recurrence occurs, such cancer becomes curable by local treatment with surgery.

Among various tumors, hepatocellular carcinoma (hereinafter referred to as HCC) is one of the most common fatal cancers in the world and the number of incidences is increasing in many countries including the USA, Japan, China and European countries. Both hepatitis B virus (hereinafter referred to as HBV) and hepatitis C virus (hereinafter referred to as HCV) infections can be a causative of HCC. In fact, increase in HCC patients is in parallel to an increase in chronic HCV infection (El-Serag, H. B. & Mason, A. C. Rising incidence of hepatocellular carcinoma in the United States, *N. Engl. J. Med.* 340, 745-750 (1999) and Okuda, K. Hepatocellular carcinoma, *J. Hepatol*, 32, 225-237 (2000)). Despite the elevated incidences of HCC, there is no promising therapy for this disease. The major problem in the treatment of HCC is intrahepatic metastasis. Recurrence was observed in 30 to 50% of HCC patients who had received hepatic resection (Iizuka, N. et al. NM23-H1 and NM23-H2 messenger RNA abundance in human hepatocellular carcinoma, *Cancer Res.* 55, 652-657 (1995), Yamamoto, J. et al. Recurrence of hepatocellular carcinoma after surgery, *Br. J. Surg.* 83, 1219-1222 (1996), and Poon, R. T. et al. Different risk factors and prognosis for early and late intrahepatic recurrence after resection of hepatocellular carcinoma, *Cancer* 89, 500-507 (2000)). Although the pathologic TNM staging system has been applied in the treatment of HCC, this system is poorly predictive of recurrences in patients who undergo hepatic resection (Izumi, R. et al. Prognostic factors of hepatocellular carcinoma in patient undergoing hepatic resection, *Gastroenterology* 106, 720-727 (1994)). A number of molecules have also been proposed as predictive markers for HCCs, none of them has proven to be clinically useful (Iizuka, N. et al. NM23-H1 and NM23-H2 messenger RNA abundance in human hepatocellular carcinoma, *Cancer Res.* 55, 652-657 (1995), Hsu, H. C. et al. Expression of p53 gene in 184 unifocal hepatocellular carcinomas: association with tumor growth and invasiveness, *Cancer Res.* 53, 4691-4694 (1993), and Mathew, J. et al. CD44 is expressed in hepatocellular carcinomas showing vascular invasion, *J. Pathol.* 179, 74-79 (1996)). Thus, any method to predict recurrence would be quite valuable to understand cancer mechanisms and also to establish the new therapies for cancer. However, because there are technological limitations for predicting recurrence by the traditional methods and further limitations may be attributable to high inter-patient heterogeneity of tumors, it is necessary to devise a novel method to characterize tumors and predict cancer recurrence.

Recent development of microarray technologies, which allow one to perform parallel expression analysis of a large number of genes, has opened up a new era in medical science (Schena, M. et al. Quantitative monitoring of gene expression patterns with a complementary DNA microarray, *Science* 270, 467-470 (1995), and DeRisi J. et al. Use of a cDNA microarray to analyze gene expression patterns in human cancer, *Nature Genet.* 14, 457-460 (1996)). In particular, studies by cDNA microarrays of the gene expression of tumors have provided significant insights into the properties of malignant tumors such as prognosis and drug-sensitivity (Alizadeh, A. A. et al. Distinct types of diffuse large B-cell lymphoma identified by gene expression profiling, *Nature* 403, 503-511 (2000), and Scherf, U. et al. A gene expression database for the molecular pharmacology of cancer, *Nature Genet.* 24, 236-244 (2000)).

Recently, supervised learning has been introduced into gene-expression analysis (Brazma, A & Vilo, J. Gene expression data analysis, *FEBS Lett.* 480, 17-24 (2000) and Kell, D. B. & King, R. D. On the optimization of classes for the assignment of unidentified reading frames in functional genomics programs: the need for machine learning, *Trends Biotechnol.* 18, 93-98 (2000)). Using classified samples, supervised learning has the conclusive advantage of much a priori knowledge about the nature of the data (Duda, R. O. et al. *Pattern classification*, John Wiley & Sons (2001), and Jain, A. K. et al. Statistical pattern recognition: A review, *IEEE Trans. Pattern Analysis and Machine Intelligence.* 22, 4-37 (2000)). However, none of supervised learning methods previously published directly evaluates the combination of genes and thus can utilize information concerning the statistical characteristics, i.e., structure of the distribution of genes (Golub, T. R. et al. Molecular classification of cancer: class discovery and class prediction by gene expression monitoring, *Science* 286, 531-537 (1999), and Brown, M. P. et al. Knowledge-based analysis of microarray gene expression data by using support vector machines, *Proc. Natl. Acad. Sci, USA* 97, 262-267 (2000)).

Scoring systems that are predictive of cancer recurrence are created by analyzing the DNA microarray data with supervised learning in statistical pattern recognition (Duda, R. O. et al. *Pattern classification*, John Wiley & Sons (2001)).

Supervised learning in statistical pattern recognition has been successfully applied to resolve a variety of issues such as document classification, speech recognition, biometric recognition, and remote sensing (Jain, A. K. et al. Statistical pattern recognition: A review, *IEEE Trans, Pattern Analysis and Machine Intelligence.* 22, 4-37 (2000)).

In the present invention, the inventors provide a scoring system to predict cancer recurrence by analyzing the expression of genes and/or proteins of human primary tumors. That is the invention concerns a method for the prediction of cancer recurrence which comprises measuring the expression of genes and/or proteins of human tumor tissues, and comparing it with the expression of the genes and/or proteins of human primary tumors from patients who have cancer recurrence and those who do not have cancer recurrence.

BRIEF DESCRIPTION OF THE DRAWINGS

FIG. 1 illustrates the procedure of gene selection (Steps 1-7) and evaluation (Steps 8-10) of the scoring system with the optimal gene subset.

DETAILED EXPLANATION OF THE INVENTION

Figure 2:
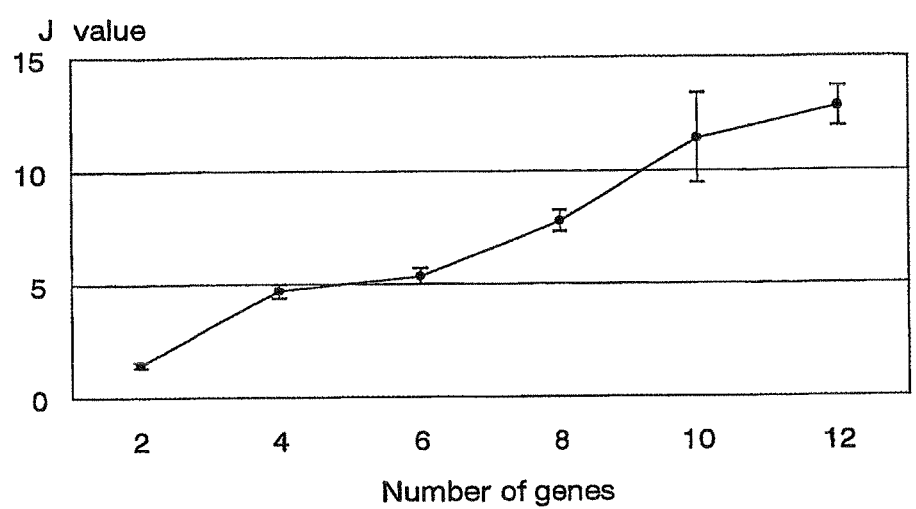
FIG. 2 illustrates the optimal number of genes.

In the present invention, human tissues from tumors including those of brain, lung, breast, stomach, liver, pancreas, gallbladder, colon, rectum, kidney, bladder, ovary, uterus, prostate, and skin are used. After human tissues are resected during surgeries, it is preferable that they are immediately frozen in liquid nitrogen or acetone containing dry ice and stored at between −70 and −80° C. until use with or without being embedded in O.C.T. compound (Sakura-Seiki, Tokyo, Japan, Catalog No. 4583).

Expression of genes and/or proteins of tumor tissues from patients who are tested for the probability of cancer recurrence are analyzed by measuring the levels of RNA and/or proteins. In many cases, the levels of RNA and/or proteins are determined by measuring fluorescence from substances including fluorescein and rhodamine, chemiluminescence from luminole, radioactivities of radioactive materials including $^3$H, $^{14}$C, $^{35}$S, $^{33}$P, $^{32}$P, and $^{125}$I, and optical densities. Expression levels of RNA and/or proteins are determined by known methods including DNA microarray (Schena, M. et al. Quantitative monitoring of gene expression patterns with a complementary DNA microarray, Science 270, 467-470 (1995), and Lipshutz, R. J. et al. High density synthetic oligonucleotide arrays, Nature Genet. 21, 20-24 (1999)), RT-PCR (Weis, J. H. et al. Detection of rare mRNAs via quantitative RT-PCR, Trends Genetics 8, 263-264 (1992), and Bustin, S. A. Absolute quantification of mRNA using real-time reverse transcription polymerase chain reaction assays, J. Mol. Endocrinol. 25, 169-193 (2000)), northern blotting and in situ hybridization (Parker, R. M. & Barnes, N. M. mRNA: detection in situ and northern hybridization, Methods Mol. Biol. 106, 247-283 (1999)), RNase protection assay (Hod, Y. A. Simplified ribonuclease protection assay, Biotechniques 13, 852-854 (1992), Saccomanno, C. F. et al. A faster ribonuclease protection assay, Biotechniques 13, 846-850 (1992)), western blotting (Towbin, H. et al. Electrophoretic transfer of proteins from polyacrylamide gels to nitrocellulose sheets, Proc. Natl. Acad. Sci. USA 76, 4350-4354 (1979), Burnette, W. N. Western blotting: Electrophoretic transfer of proteins form sodium dodecyl sulfate-polyacrylamide gels to unmodified nitrocellulose and radioiodinated protein A, Anal. Biochem. 112, 195-203 (1981)), ELISA assays (Engvall, E. & Perlman, P. Enzyme-linked immunosorbent assay (ELISA): Quantitative assay of immunoglobulin G, Immunochemistry 8: 871-879 (1971)), and protein arrays (Merchant, M. & Weinberger, S. R. Review: Recent advancements in surface-enhanced laser desorption/ionization-time of flight-mass spectrometry, Electrophoresis 21, 1164-1177 (2000), Paweletz, C. P. et al. Rapid protein display profiling of cancer progression directly from human tissue using a protein biochip, Drug Development Research 49, 34-42 (2000)).

Expression of genes and/or proteins of tumors from cancer patients who have early recurrence and those who do not are determined in the same way as that for the patients who are tested for the probability of recurrence.

Although early recurrence of cancer varies among different cancer types, it usually occurs within one or two years after resection. Therefore, tumors from cancer patients who have recurrence within one or two years after resection can be used as the tumors of patients with early recurrence, and those from patients who do not have recurrence before one or two years after resection can be used as the tumors of patients without early recurrence.

Differences in the expression levels or patterns of genes and/or proteins of tumors between cancer patients who have early recurrence and who do not can be analyzed and detected by known methods of statistical analyses. Supervised learning in statistical pattern recognition can be used for statistical analysis of the expression patterns of genes and/or proteins of tumors. By supervised learning in statistical pattern recognition, 2 or more of genes and/or proteins of which expression is indicative of cancer recurrence are selected from the examined genes and/or proteins.

Some genes and/or proteins that are indicative of cancer recurrence are first selected by one-dimensional criteria. Then, the optimal subsets of genes and/or proteins are selected out of these genes and/or proteins by an exhaustive search with the leave-one-out method that can take all the possible combinations of genes and/or proteins into account.

Formulae that are predictive of cancer recurrence are created by using the optimal subsets of at least 2 or more of genes and/or proteins, preferably 4 or more of genes and/or proteins, more preferably 6 or more of genes and/or proteins, and most preferably 12 or more of genes and/or proteins of which expression is indicative of cancer recurrence. Simple classifiers such as linear classifier (Duda, R. O. et al. Pattern classification, John Wiley & Sons (2001), and Jain, A. K. et al. Statistical pattern recognition: A review, IEEE Trans. Pattern Analysis and Machine Intelligence. 22, 4-37 (2000)) that work well even if the number of samples is small compared to the number of genes and/or proteins are used to create formulae.

The present invention also concerns kits to carry out the methods of the present invention. Kits to examine the expression patterns of 2 or more of genes and/or proteins that are indicative of cancer recurrence consist of the components including reagents for RNA extraction, enzymes for the syntheses of cDNA and cRNA, DNA chip, oligonucleotide chip, protein chip, probes and primers for the analyses, DNA fragments of control genes, and antibodies to various proteins.

Components of the kits are easily available from the market. For instance, oligonucleotide chips, guanidine-phenol reagent, reverse transcriptase, T7 RNA polymerase and taq polymerase can be purchased and assembled for the kits of the present invention.

The following examples merely illustrate the preferred method for the prediction of cancer recurrent of the present invention and are not to be construed as being limited thereto.

EXAMPLES

Example 1

Selection of the Patients for Analysis of Early Intrahepatic Recurrence

It has been reported that early intrahepatic recurrences (within one year) after surgery arise mainly from intrahepatic metastases, whereas late recurrences are more likely to be multicentric occurrence (Poon, R. T. et al. Different risk factors and prognosis for early and late intrahepatic recurrence after resection of hepatocellular carcinoma, Cancer 89, 500-507 (2000)). Moreover, it is well known that the outcome of patients with intrahepatic recurrence was worse than that of patients with multicentric occurrence (Yamamoto, J. et al. Recurrence of hepatocellular carcinoma after surgery, Br. J. Surg. 83, 1219-1222 (1996), and Poon, R. T. et al. Different risk factors and prognosis for early and late intrahepatic recurrence after resection of hepatocellular carcinoma, Cancer 89, 500-507 (2000)). Therefore gene-expression patterns linked to early intrahepatic recurrence were investigated within one year after surgery.

Thirty-three patients underwent surgical treatment for HCC in Yamaguchi University Hospital between May 1997 and January 2000. Informed consent in writing was obtained from all cases before surgery. The study protocol was approved by the Institutional Review Board for Human Use at the Yamaguchi University School of Medicine in May 1996. A histopathological diagnosis of HCC was made in all patients after surgery. The histopathological examination also revealed no residual tumors (R0) in all of the 33 HCC samples. Table 1 shows the clinicopathologic characteristics of the 33 patients, based on the TNM classification of Union Internationale Contre le Cancer (UICC) (Sobin, L. H. & Wittekind, C. TNM classification of Malignant Tumors, 5th ed., UICC, Wiley-Liss, 74-77 (1997)). Serologically, 7 patients were hepatitis B surface antigen-positive, 22 patients were anti-HCV antibody-positive, and the remaining 4 patients were negative for both. The 33 patients were tracked for cancer recurrence with ultrasonography, computed tomography, and alpha-fetoprotein level every 3 months following hepatic resection. Whenever necessary, magnetic resonance imaging and hepatic angiography were added. Of the 33 HCC patients, early intrahepatic recurrences were found in 12 (36%). In 11 of the 12 patients, recurrent HCCs were detected as multiple nodules or diffuse dissemination in the remnant liver. In one patient, a novel tumour was detected as single nodule in the segment adjacent to the resected primary lesion 9 month after surgery, and then multiple lung metastases were observed. None of the remaining 21 patients had intrahepatic recurrences and other distant metastases within one year after surgery. These patients were divided into two groups; the patients who had intrahepatic recurrences within one year in Group A (n=12) and those who did not in Group B (n=21) (Table 1). The $\chi^2$ test and Fisher's exact test were used to elucidate differences in clinicopathologic factors between the 2 groups.

Example 2

Extraction of the RNA from Tissues

Pieces of the tissues (about 125 mm$^3$) were suspended in TRIZOL (Life Technologies, Gaithersburg, USA, Catalog No. 15596-018) or Sepasol-RNAI (Nacalai tesque, Kyoto, Japan, Catalog No. 306-55) and homogenized twice with a Polytron (Kinematica, Littau, Switzerland) (5 sec. at maximum speed). After addition of chloroform, the tissues homogenates were centrifuged at 15,000×g for 10 min, and aqueous phases, which contained RNA, were collected. Total cellular RNA was precipitated with isopropyl alcohol, washed once with 70% ethanol and suspended in DEPC-treated water (Life Technologies, Gaithersburg, USA, Catalog No. 10813-012). After RNA was treated with 1.5 units of DNase I (Life Technologies, Gaithersburg, USA, Catalog No. 18068-015), the RNA was re-extracted with TRIZOL/chloroform, precipitated with ethanol and dissolved in DEPC-treated water. Thereafter, small molecular weight nucleotides were removed by using RNeasy Mini Kit (QIAGEN, Hilden, Germany, Catalog No. 74104) according to a manufacture's instruction manual, Quality of the total RNA was judged from ratio of 28S and 18S ribosomal RNA after agarose gel electrophoresis. The purified total RNA was stored at −80° C. in 70% ethanol solution until use.

Example 3

Synthesis of cDNA and Labeled cRNA Probes cDNA was synthesized by using reverse Super-Script Choice System (Life Technologies, Gaithersburg, USA, Catalog No. 18090-019) according to the manufacture's instruction manual. Five microgram of the purified total RNA was hybridized with an oligo-dT primer (Sawady Technology, Tokyo, Japan) that contained the sequences for the T7 promoter and 200 units of SuperScriptII reverse transcriptase and incubated at 42° C. for 1 hr. The resulting cDNA was extracted with phenol/chloroform and purified with Phase Lock Gel Light (Eppendorf, Hamburg, Germany, Catalog No. 0032 005.101).

cRNA was also synthesized by using MEGAscript T7 kit (Ambion, Austin, USA, Catalog No. 1334) and the cDNA as templates according to the manufacture's instruction. Approximately 5 μg of the cDNA was incubated with 2 μl of enzyme mix containing T7 polymerase, 7.5 mM each of adenosine triphosphate (ATP) and guanosine triphosphate (GTP), 5.625 mM each of cytidine triphosphate (CTP) and uridine triphosphate (UTP), 1.875 mM each of Bio-11-CTP and Bio-16-UTP (ENZO Diagnostics, Farmingdale, USA, Catalog No. 42818 and 42814, respectively) at 37° C. for 6 hr. Mononucleotides and short oligonucleotides were removed by column chromatography on CHROMA SPIN+STE-100 column (Clontech, Palo Alto, USA, Catalog No. K1302-2), and the cRNA in the eluates was sedimented by adding ethanol. Quality of the cRNA was judged from the length of the cRNA after agarose gel electrophoresis. The purified cRNA was stored at −80° C. in 70% ethanol solution until use.

Example 4

Gene Expression Analysis of Tumors from Patients with and without Recurrence

Gene expression of human primary tumors from live cancer patients were examined by high-density oligonucleotide microarrays (HuGeneFL array, Affymetrix, Santa Clara, USA, Catalog No. 510137) (Lipshutz, R. L. et al. High density synthetic oligonucleotide arrays, *Nature Genet.* 21, 20-24 (1999)). For hybridization with oligonucleotides on the chips, the cRNA was fragmented at 95° C. for 35 min in a buffer containing 40 mM Tris (Sigma, St. Louis, USA, Catalog No. T1503)-acetic acid (Wako, Osaka, Japan, Catalog No. 017-00256) (pH8.1), 100 mM potassium acetate (Wako, Osaka, Japan, Catalog No. 160-03175), and 30 mM magnesium acetate (Wako, Osaka, Japan, Catalog No. 130-00095). Hybridization was performed in 200 µl of a buffer containing 0.1M 2-(N-Morpholino) ethanesulfonic acid (MES) (Sigma, St. Louis, USA, Catalog No. M-3885) (pH6.7), 1M NaCl (Nacalai tescque, Tokyo, Japan, Catalog No. 313-20), 0.01% polyoxylene(10)octylphenyl ether (Wako, Osaka, Japan, Catalog No. 168-11805), 20 µg herring sperm DNA (Promega, Madison, USA, Catalog No. D181B), 100 µg acetylated bovine serum albumin (Sigma, St. Louis, USA, Catalog No. B-8894), 10 µg of the fragmented cRNA, and biotinylated-control oligonucleotides, biotin-5'-CTGAACG-GTAGCATCTTGAC-3' (SEQ ID NO: 1) (Sawady technology, Tokyo, Japan) at 45° C. for 12 hr. After washing the chips with a buffer containing 0.01M MES (pH6.7), 0.1M NaCl, 0.001% polyoxylene(10)octylphenyl ether buffer, the chips were incubated with biotinylated anti-streptavidin antibody (Funakoshi, Tokyo, Japan, Catalog No. BA0500) and staining with streptavidin R-Phycoerythrin (Molecular Probes, Eugene, USA, Catalog No. S-866) to increase hybridization signals as described in the instruction manual (Affymetrix, Santa Clara, USA). Each pixel level was collected with laser scanner (Affymetrix, Santa Clara, USA) and levels of the expression of each cDNA and reliability (Present/Absent call) were calculated with Affymetrix GeneChip ver.3.3 and Affymetrix Microarray Suite ver.4.0 softwares. From these experiments, expression of 6000 genes in the human primary tumors of liver cancer patients are determined.

Example 5

Kinetic RT-PCR Analysis

Expression of genes is also determined by kinetic RT-PCR. Kinetic RT-PCR was performed by a real-time fluorescence PCR system. PCR amplification using a Light-Cycler instrument (LightCycler system, Roche Diagnostics, Mannheim, Germany, Catalog No. 2011468) was carried out in 20 µl of reaction mixture consisting of a master mixture and buffer (LightCycler DNA Master hybridization probes, Roche Diagnostics, Mannheim, Germany, Catalog No. 2158825), 4 mM magnesium chloride (Nacalai teseque, Tokyo, Japan, Catalog No. 7791-18-6), 10 pmoles of PCR primers (Sawady Technology, Tokyo, Japan), 4 pmoles of fluorescent hybridization probes (Nihon Genome Research Laboratories, Sendai, Japan), which were designed to hybridize with the target sequences in a head-to-tail arrangement on the strand of amplified products, and 2 µl of template cDNA in a LightCycler capillary (Roche Diagnostics, Mannheim, Germany, Catalog No. 1909339). The donor probes was labeled at the 3'-end with fluorescence, while the acceptor probe was labeled at the 5'-end with LC-Red640 and modified at the 3'-end by phosphorylation to block extension. The gap between the 3'-end of the donor probe and the 5'-end of the acceptor probe was between 1 and 3 bases. Prior to amplification, 0.16 µl of TaqStart antibody (Clontech, Palo Alto, USA, Catalog No. 5400-1) was added to the reaction mixture, which was followed by the incubation at room temperature for 10 min to block primer elongation. Then, the antibody was inactivated by the incubation at 95° C. for 90 sec., and the amplification was performed in the LightCycler by 40 cycles of incubation at 95° C. for 0 sec. for denaturation, at 57-60° C. for 3-10 sec. for annealing and at 72° C. for 10 sec. for extension, with a temperature slope of 20° C./sec. Real-time PCR monitoring was achieved by measuring the fluorescent signals at the end of the annealing phase in each amplification cycle. To qualify the integrity of isolated RNA and normalize the copy number of target sequences, kinetic RT-PCR analysis for glyceraldehyde-3-phosphate dehydrogenase (GAPDH) was also carried out by using hybridization probes. External standards for the target mRNA and GAPDH mRNA were prepared by 10-fold serial dilutions ($10^3$ to $10^8$) of plasmid DNA. Quantification of mRNA in each sample was performed automatically by reference to the standard curve constructed at each time point according to the LightCycler software (LightCycler software version 3, Roche Diagnostics, Mannheim, Germany).

Example 6

Identification of Sets of Genes of which Expression Distinguishes the Liver Cancer Patients Who have Early Intrahepatic Recurrence From Those the Patients Who do not have Early Intrahepatic Recurrence Early intrahepatic recurrence tended to be associated with the number of primary tumor and TNM stage with the p values of 0.041 and 0.006, respectively, but not with the other clinicopathologic factors (Table 1). The number of primary tumors at the time of surgery distinguished group A from group B only with the limited sensitivity and specificity (62% and 75%, respectively). The TNM staging also had a limited sensitivity (67%) and specificity (83%) for the separation of groups A and B. Thus, it appears that these traditional classifications cannot be predictive of the early intrahepatic recurrence.

Supervised learning in statistical pattern recognition was applied to analyze the data of high-density oligonucleotide microarrays. The scoring system was designed with the training samples and was validated its performance with the test samples (FIG. 1). In order to maintain independence of the training and test samples, the cross-validation approach in which the training and the test samples were interchanged was adopted. Thirty-three available samples were divided into 30 training samples and 3 test samples by the cross-validation approach (FIG. 1, Step 1). On the basis of a prior probability, ten sets of the training samples consisting of 11 samples from Group A and 19 samples from Group B were created. As a result, ten sets of three test samples consisting of one from Group A and two from Group B were created.

Fifty useful genes were selected to create the predictive scoring system from all the examined genes that had mean average differences of more than twofold between Group A and B using the Fisher criterion (FIG. 1, Steps 2-3), which was given by the following Formula (I), $$F(i) = \frac{(\mu_A(i) - \mu_B(i))^2}{P(A)\sigma_A^2(i) + P(B)\sigma_B^2(i)}$$

where $\mu_A(i)$ is the i th component of the sample mean vector $\mu_A$ of Group A, $\sigma_A^2(i)$ is the i th diagonal element of the sample covariance matrix $\Sigma_A$ of Group A, and P(A) is the a priori probability of Group A.

Then, the optimal subset of the genes for the scoring system was identified as mentioned below.

The Fisher linear classifier assigns a test sample x to be classified to Group A in the following Formula (II).

if $F_A(x) < F_B(x)$ where $$F_A(x) = \frac{1}{2}(x - \mu_A)^T \sum_w^{-1}(x - \mu_A) - \ln P(A)$$

$$\sum_w = P(A)\sum_A + P(B)\sum_B$$

In the leave-one-out method, the sample mean vector, sample covariance matrix, and the a priori probability were estimated by using 29 samples as training samples. Then, the resulting Fisher linear classifier was tested on the remaining sample as a pseudo-test sample. This operation was repeated 30 times. The error rate was calculated for each possible subset of the genes. For example, when selecting 5 genes out of 50, the number of subsets to be examined is two million.

Next, candidate gene subsets minimizing the error rate were selected (FIG. 1, Step 4). This trial was independently repeated 10 times (FIG. 1, Step 5).

Among the candidate gene subsets, the gene subset that most frequently appeared throughout the 10 trials was selected as the optimal subset of the genes for the discrimination of the two groups (FIG. 1, Step 6). Using the optimal subset of genes selected, the score T is given by the following Formula (III).

$$T(x) = F_A(x) - F_B(x)$$

In this scoring system, all HCCs with a negative T value are classified into Group A (early intrahepatic recurrence group) and all HCCs with a positive T value are classified into Group B (nonrecurrence group).

The optimal number of the genes was determined according to the criterion J that was given by the following formula (V) (FIG. 1, Step 7).

$$J = \frac{1}{30}\left[\sum_{x \in B} T(x) - \sum_{x \in A} T(x)\right]$$

The criterion J measures the separability of Group A from B. The average and 95% confidence interval of the J values in 10 different training sets were computed for various numbers of the genes (FIG. 2). The separability became better in parallel to an increase in the number of the genes. Ninety-five percentage of the confidence interval became almost similar when the number of the genes reached 10 and 12, indicating that the 12 is the most appropriate number of the genes for the separability of the two groups (FIG. 2).

Example 7

Figure 3:
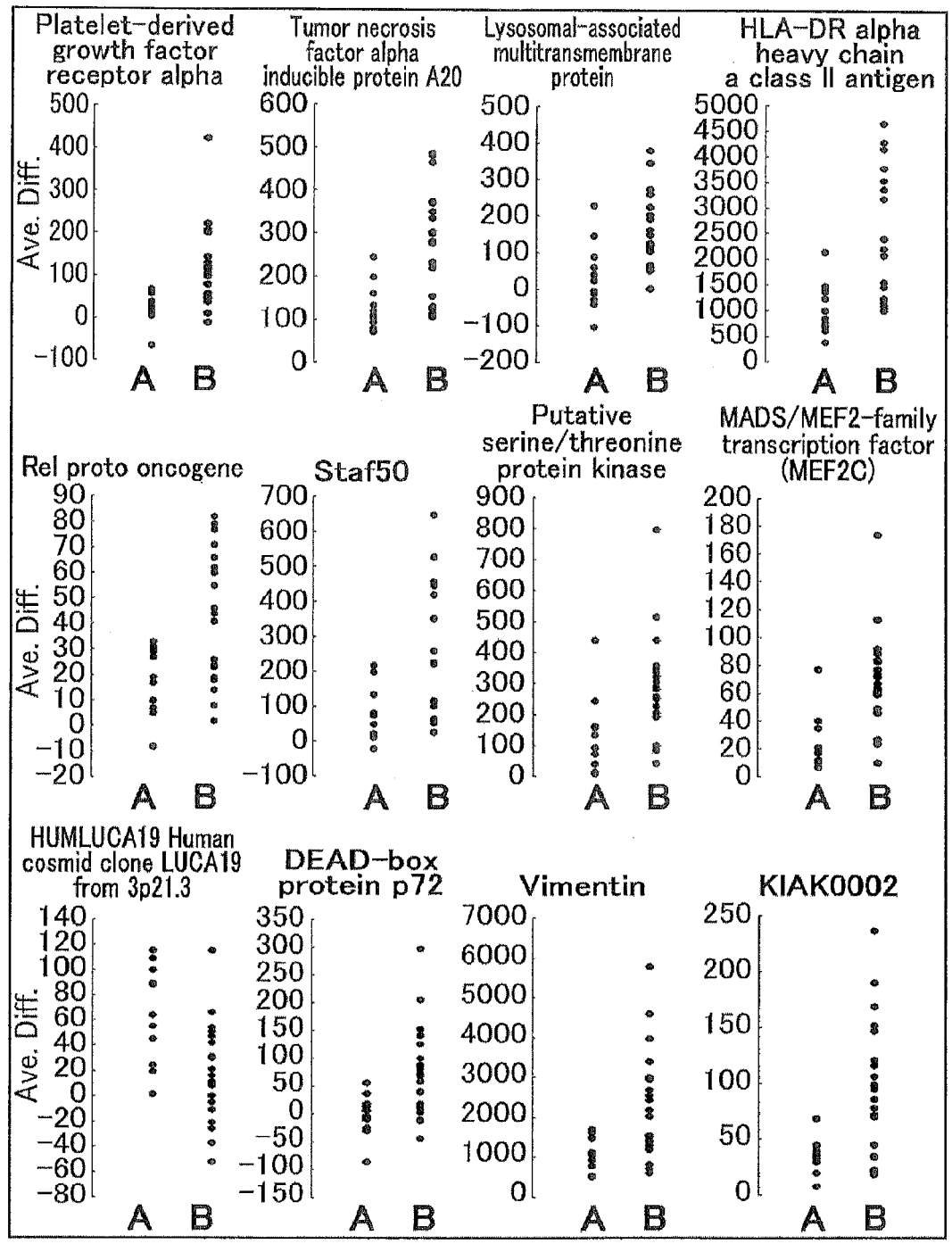
FIG. 3 illustrates the average differences of the mRNA for the genes selected for the prediction of early intrahepatic recurrence. The average differences of the mRNA for the 12 genes were compared between Group A (indicated as A) and Group B (indicated as B).
Figure 4:
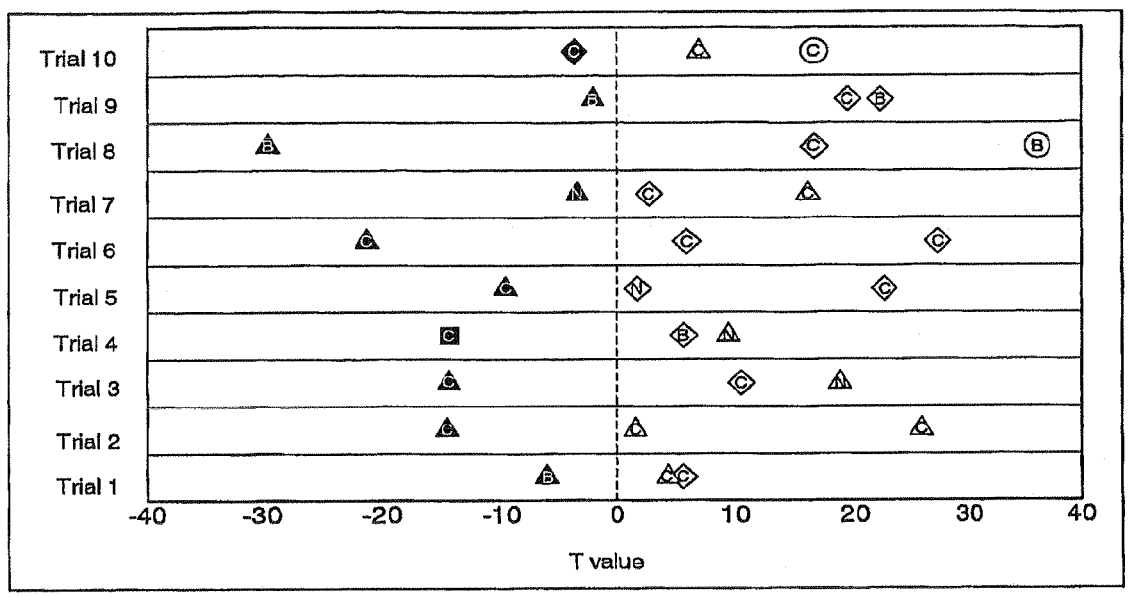
FIG. 4 illustrates the relation between virus type, TNM stage, and scores (T values) for the prediction of early intrahepatic recurrence. Using the optimal subset of 12 genes, the scoring system created with 30 training samples was evaluated with 3 test samples. This operation was independently repeated 10 times. The T values for all of the test sample were calculated. Early intrahepatic recurrence was predicted when the T value is below zero. Regardless of stage and virus types, all HCCs with a negative T value had early intrahepatic recurrences and all HCCs with a positive T value had no recurrences. Filled, Group A (patients with early intrahepatic recurrence); White, Group B (patients without early intrahepatic recurrence); O, stage I; ◇; stage II; Δ, stage IIIA; □, stage IVA. B; HBV-positive, C; HCV-positive, N; HBV-HCV-double negative.
Figure 5:
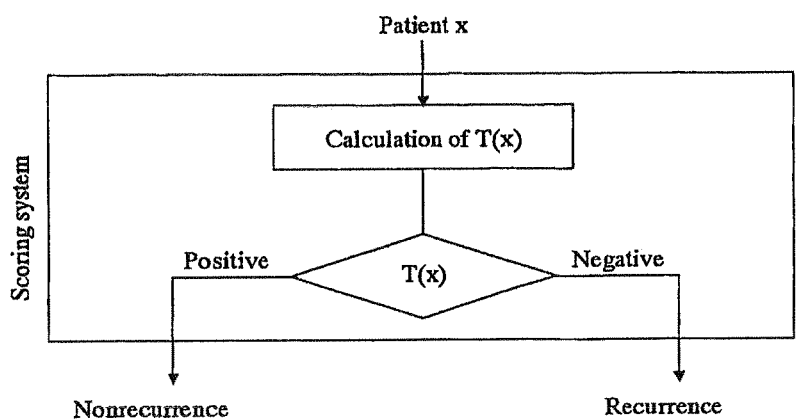
FIG. 5 illustrates the scoring system.

The Optimal Subset of the 12 Genes of which Expression is Indicative of Early Intrahepatic Recurrence According to the algorithm described above, the optimal subset of the 12 genes that discriminates Group A from Group B was identified. The optimal gene subset consisted of the genes for platelet-derived growth factor receptor alpha (PDGFRA), tumor necrosis factor alpha (TNF-α) inducible protein A20, lysosomal-associated multitransmembrane protein (LAPTm5), HLA-DR alpha heavy chain, rel proto-oncogene, Staf50, putative serine/threonine protein kinase, MADS/MEF2-family transcription factor (MEF2C), HUMLUCA19 Human cosmid clone LUCA19 from 3p21.3, DEAD-box protein p72, vimentin and KIAK0002 (Table 2). Of the 12 genes selected, expression of the eleven were down-regulated in Group A; the mean of the average differences of these genes in Group A were less than half of those in Group B (FIG. 3). In contrast, the HUMLUCA19 gene expression was up-regulated in Group A, the mean of the average differences of the HUMLUCA19 gene in Group A was increased by more than 3-fold compared to that in Group B (FIG. 3). Accuracy of the scoring for the prediction of the early intrahepatic was evaluated with the 10 different sets of 3 test samples (FIG. 4). Early recurrence of HCC is predicted by calculating the T values of the 12 genes from HCC patients. Recurrence within one year after surgery is very likely when the T value is below zero, and recurrence within one year after surgery is quite unlikely when the T value is above zero. The scoring system could perfectly predict early intrahepatic recurrence of 3 test samples in all 10 trials (FIG. 4). The scoring system was independent of viral infection patterns and was much more accurate than TNM staging system (FIG. 4). Scoring system based on all 33 HCCs with the above 12 genes (FIG. 5) includes the following formula (V).

$T(x) = 0.053862x_1 + 0.038848x_2 + 0.030176x_3 + 0.001824x_4 + 0.096997x_5 + 0.017259x_6 + 0.015908x_7 + 0.103081x_8 - 0.093746x_9 + 0.024031x_{10} - 0.005417x_{11} - 0.119177x_{12} - 11.046007,$ where $x_1, x_2, x_3, x_4, x_5, x_6, x_7, x_8, x_9, x_{10}, x_{11}, x_{12}$, are the normalized average differences of the mRNAs for platelet-derived growth factor receptor alpha (PDGFRA), tumor necrosis factor alpha (TNF-α) inducible protein A20, lysosomal-associated multitransmembrane protein (LAPTm5), HLA-DR alpha heavy chain, rel proto-oncogene, Staf50, putative serine/threonine protein kinase, MADS/MEF2-family transcription factor (MEF2C), HUM-LUCA19 Human cosmid clone LUCA19 from 3p21.3, DEAD-box protein p72, vimentin and the KIAK0002 gene (Table 2).

The 12 genes selected by the present invention are involved in a wide range of biological processes. Of these, immune response-related genes such as HLA-DR alpha heavy chain, TNF-α inducible protein A20 and Staf50, were down-regulated in HCCs with early intrahepatic recurrence. Because HLA-DR alpha heavy chain is considered to play an important role in the antigen-presenting by macrophages (Tissot, C. & Mechti N. Molecular cloning of a new interferon-induced factor that represses human immunodeficiency virus type 1 long terminal repeat expression, *J. Biol. Chem.* 270, 14891-14898 (1995)), its down-regulation in tumorous tissues might facilitate escape of tumor cells from host immune surveillance. Rel proto-oncogene, which is involved in intracellular signaling pathway as well as NF-κB, was also down-regulated in HCCs with early intrahepatic recurrence. Furthermore, the expression of rel/NF_κB have been reported to be associated with T-cell activation (Mora, A et al. NF-kappa B/Rel participation in the lympholine-dependent proliferation of T lymphoid cells, *J. Immunol.* 166, 2218-2227 (2000)). Thus, it seems that several genes that were selected for the use to predict early intrahepatic recurrence by the present invention are involved in the weakening the host immune responses against HCC cells possessing high metastatic potentials.

Gene expression pattern of other HCC patients whose follow-up period recently reached one year was also analyzed by oligonucleotide microarray, and the scores of the expression of 12 genes were calculated according to the formula described above. T values of patients who lived without recurrence more than one year after surgery were positive (plus score) and that of the other patient who had intrahepatic recurrence within one year after surgery was negative (minus). Thus, the scoring system consisting of the subset of 12 genes obtained from 6000 could predict early intrahepatic recurrence accurately. The application of supervised learning in statistical pattern recognition to clinical specimens may provide a key information in advances for prevention, diagnosis, and therapeutics of other diseases as well as HCC. Furthermore, not only DNA microarray but also other methods such as RT-PCR can be used to determine the expression of the optimal sets of genes.

TABLE 1

Clinicopathologic factors of the HCCs used to the early intrahepatic recurrence.

| Factors | Group A (n = 12) | Group B (n = 21) | P value |
|---|---|---|---|
| Sex | | | N.S. |
| Male | 8 | 16 | |
| Female | 4 | 5 | |
| Age | | | N.S. |
| < or = to 60 | 5 | 7 | |
| >60 | 7 | 14 | |
| Viral Infection | | | N.S. |
| HBV | 3 | 4 | |
| HCV | 8 | 14 | |
| Non B, Non C | 1 | 3 | |
| Primary lesion | | | N.S. |
| Single tumor | 3 | 13 | |
| Multiple tumors | 9 | 8 | |
| Tumor size (cm) | | | N.S. |
| <2.0 | 0 | 5 | |
| 2.0-5.0 | 8 | 14 | |
| >5.0 | 4 | 2 | |
| Stage* | | | 0.006 |
| I/II | 2 | 14 | |
| IIIA/IVA | 10 | 7 | |
| Histological grading* | | | N.S. |
| G1 | 0 | 2 | |
| G2 | 9 | 17 | |
| G3 | 3 | 2 | |
| Venous invasion* | | | N.S. |
| (−) | 7 | 18 | |
| (+) | 5 | 3 | |
| Non-tumorous liver | | | N.S. |
| Non-specific change | 1 | 1 | |
| Chronic heptasis | 2 | 10 | |
| Liver cirrhosis | 9 | 10 | |

*Assessment based on TNM classification of UICC HBV: hepatitis B virus, HCV: hepatitis C virus, non-B non-C; neither HBV nor HCV Group A: early intrahepatic recurrence (+), Group B: early intrahepatic recurrence (−) N.S.: Not significant.

TABLE 2

The formula and the 12 genes to predict early intrahepatic recurrence.
Formula $T(x) = 0.053862x_1 + 0.038848x_2 + 0.030176x_3 + 0.001824x_4 + 0.096997x_5 + 0.017259x_6 + 0.015908x_7 + 0.103081x_8 - 0.093746x_9 + 0.024031x_{10} - 0.005417x_{11} - 0.119177x_{12} - 11.046007$

| | GB* | Description |
|---|---|---|
| $x_1$; | M21574 | platelet-derived growth factor receptor alpha (PDGFRA) |
| $x_2$; | M59465 | tumor necrosis factor alpha inducible protein A20 |
| $x_3$; | U51240 | lysosomal-associated multitransmembrane protein (LAPtm5) |
| $x_4$; | X00274 | HLA-DR alpha heavy chain (class II antigen) |
| $x_5$; | X75042 | rel proto-oncogene |
| $x_6$; | X82200 | Staf50 |
| $x_7$; | Y10032 | putative serine/threonine protein kinase |
| $x_8$; | L08895 | MADS/MEF2-family transcription factor (MEF2C) |
| $x_9$; | AC000063 | HUMLUCA19 Human cosmid clone LUCA19 from 3p21.3 |
| $x_{10}$; | U59321 | DEAD-box protein p72 |
| $x_{11}$; | Z19554 | vimentin |
| $x_{12}$; | D13639 | KIAK0002 gene |

GB*: gene bank access number

What is claimed is:

1. A kit for determining expression levels in a sample from an hepatocellular carcinoma (HCC) patient of at least ten genes indicative of recurrence of HCC in the patient comprising, one or more components for determining the expression levels of said at least ten genes, wherein said one or more components are selected from the group consisting of: a DNA array chip, an oligonucleotide array chip, a protein array chip, an antibody, a plurality of probes; and a set of primers, and wherein said at least ten genes are selected from the group consisting of:
   (1) platelet-derived growth factor receptor alpha;
   (2) tumor necrosis factor alpha inducible protein A20;
   (3) lysosomal-associated multitransmembrane protein (LAPTm5);
   (4) HLA-DR alpha heavy chain;
   (5) rel proto-oncogene;
   (6) Staf50;
   (7) putative serine/threonine protein kinase;
   (8) MADS/MEF2-family transcription factor (MEF2C);
   (9) HUMLUCA19 Human cosmid clone LUCA19 from 3p21.3;
   (10) DEAD-box protein p72;
   (11) vimentin; and
   (12) KIAK0002; each as set forth in Table 2.

2. The kit of claim 1, wherein said one or more components determine the expression levels of all 12 genes indicative of recurrence of HCC.

3. The kit of claim 1, further comprising one or more reagents for RNA extraction; one or more enzymes for syntheses of cDNA and cRNA; one or more reagents for hybridization for DNA chip, oligonucleotide chip, protein chip, western blot, probes, or primers; one or more reagents for binding of said antibodies to proteins indicative of recurrence of cancer; or DNA fragments of control genes.

4. The kit of claim 1, further including instructions for determining the likelihood of recurrence of HCC based on the expression levels of the at least ten genes indicative of recurrence of HCC.

5. The kit of claim 4, wherein said instructions include a formula to determine the likelihood of recurrence of HCC based upon the expression levels of the at least ten genes indicative of recurrence of HCC.

6. The kit of claim 5, wherein said formula is $$T(x)=0.053862\chi_1+0.038848\chi_2+0.030176\chi_3+0.001824\chi_4+0.096997\chi_5+0.017259\chi_6+0.015908\chi_7+0.103081\chi_8-0.093746\chi_9+0.024031\chi_{10}-0.005417\chi_{11}-0.119177\chi_{12}-11.046007,$$

wherein $\chi_1$ through $\chi_{12}$ are the normalized average differences of mRNAs expression levels for said genes (1) through (12), respectively, as listed in claim 1, wherein the likelihood of recurrence of HCC is determined by the T value, and wherein a positive T value indicates non-recurrence and a negative T value indicates recurrence of HCC.

7. A kit for determining expression levels in a sample from an hepatocellular carcinoma (HCC) patient of at least ten genes indicative of recurrence of hepatocellular carcinoma (HCC) comprising, an oligonucleotide array chip, said oligonucleotide array chip comprising a plurality of oligonucleotides for effecting determination of the expression levels of the at least ten genes indicative of recurrence of HCC, wherein the at least ten genes indicative of recurrence of HCC are selected from the group consisting of:
   (1) platelet-derived growth factor receptor alpha;
   (2) tumor necrosis factor alpha inducible protein A20;
   (3) lysosomal-associated multitransmembrane protein (LAPTm5);
   (4) HLA-DR alpha heavy chain;
   (5) rel proto-oncogene;
   (6) Staf50;
   (7) putative serine/threonine protein kinase;
   (8) MADS/MEF2-family transcription factor (MEF2C);
   (9) HUMLUCA19 Human cosmid clone LUCA19 from 3p21.3;
   (10) DEAD-box protein p72;
   (11) vimentin; and
   (12) KIAK0002; each as set forth in Table 2.

8. The kit of claim 7, wherein said oligonucleotide array chip comprises a plurality of oligonucleotides for effecting determination of expression levels of 12 genes indicative of recurrence of HCC listed in claim 7.

9. The kit of claim 7, further comprising one or more reagents for RNA extraction; one or more enzymes for syntheses of cDNA and cRNA; one or more reagents for hybridization for DNA chip, oligonucleotide chip, protein chip, western blot, probes, or primers; one or more reagents for binding of said antibodies to proteins indicative of recurrence of cancer; or DNA fragments of control genes.

10. The kit of claim 7, further including instructions for determining the likelihood of recurrence of HCC based on the expression levels of the at least ten genes indicative of recurrence of HCC.

11. The kit of claim 10, wherein said instructions comprise a formula to determine the likelihood of recurrence of HCC.

12. The kit of claim 11, wherein said formula is:

$$T(x)=0.053862\chi_1+0.038848\chi_2+0.030176\chi_3+0.001824\chi_4+0.096997\chi_5+0.017259\chi_6+0.015908\chi_7+0.103081\chi_8-0.093746\chi_9+0.024031\chi_{10}-0.005417\chi_{11}-0.119177\chi_{12}-11.046007,$$

wherein $\chi_1$ through $\chi_{12}$ are the normalized average differences of mRNAs expression levels for said genes (1) through (12), respectively, as listed in claim 7, wherein the likelihood of recurrence of HCC is determined by the T value, and wherein a positive T value indicates non-recurrence and a negative T value indicates recurrence of HCC.

13. A kit for determining expression levels in a sample from an hepatocellular carcinoma (HCC) patient of genes indicative of recurrence of HCC in the patient comprising, one or more components for determining the expression levels of said genes, wherein said one or more components are selected from the group consisting of: a DNA array chip, an oligonucleotide array chip, a protein array chip, an antibody, a plurality of probes; and a set of primers, and wherein said genes indicative of recurrence of HCC comprise:
   (1) platelet-derived growth factor receptor alpha;
   (2) tumor necrosis factor alpha inducible protein A20;
   (3) lysosomal-associated multitransmembrane protein (LAPTm5);
   (4) HLA-DR alpha heavy chain;
   (5) rel proto-oncogene;
   (6) Staf50;
   (7) putative serine/threonine protein kinase;
   (8) MADS/MEF2-family transcription factor (MEF2C);
   (9) HUMLUCA19 Human cosmid clone LUCA19 from 3p21.3;
   (10) DEAD-box protein p72;
   (11) vimentin; and
   (12) KIAK0002; each as set forth in Table 2.

14. The kit of claim 13, further comprising one or more reagents for RNA extraction; one or more enzymes for syntheses of cDNA and cRNA; one or more reagents for hybridization for DNA chip, oligonucleotide chip, protein chip, western blot, probes, or primers; one or more reagents for binding of said antibodies to proteins indicative of recurrence of cancer; or DNA fragments of control genes.

15. The kit of claim 13, further including instructions for determining the likelihood of recurrence of HCC based on the expression levels of said genes indicative of recurrence of HCC.

16. The kit of claim 15, wherein said instructions include a formula for determining the likelihood of recurrence of HCC based on the expression levels of said genes indicative of recurrence of HCC.

17. The kit of claim 16, wherein said formula is $$T(x)=0.053862\chi_1+0.038848\chi_2+0.030176\chi_3+0.001824\chi_4+0.096997\chi_5+0.017259\chi_6+0.015908\chi_7+0.103081\chi_8-0.093746\chi_9+0.024031\chi_{10}-0.005417\chi_{11}-0.119177\chi_{12}-11.046007,$$

wherein $\chi_1$ through $\chi_{12}$ are the normalized average differences of mRNAs expression levels for said genes (1) through (12), respectively, as listed in claim 13, wherein the likelihood of recurrence of HCC is determined by the T value, and wherein a positive T value indicates non-recurrence and a negative T value indicates recurrence of HCC.

18. The kit of claim 1, consisting essentially of the components for detecting the 10 or more genes, instructions for determining the likelihood of recurrence of HCC based on the expression levels of the at least ten genes indicative of recurrence of HCC, and, optionally, one or more reagents selected from: reagents for RNA extraction; one or more enzymes for syntheses of cDNA and cRNA; one or more reagents for hybridization for DNA chip, oligonucleotide chip, protein chip, western blot, probes, or primers; one or more reagents for binding of said antibodies to proteins indicative of recurrence of cancer; or DNA fragments of control genes.

19. A system comprising a non-transient computer-readable storage medium that provides instructions that, if executed by a processor, causes the processor to perform steps comprising:

accepting data representing gene expression levels in a sample from a hepatocellular carcinoma (HCC) patient of at least 10 genes indicative of recurrence of HCC in the patient, wherein said genes indicative of recurrence of HCC comprise:

(1) platelet-derived growth factor receptor alpha;
(2) tumor necrosis factor alpha inducible protein A20;
(3) lysosomal-associated multitransmembrane protein (LAPTm5);
(4) HLA-DR alpha heavy chain;
(5) rel proto-oncogene;
(6) Staf50;
(7) putative serine/threonine protein kinase;
(8) MADS/MEF2-family transcription factor (MEF2C);
(9) HUMLUCA19 Human cosmid clone LUCA19 from 3p21.3;
(10) DEAD-box protein p72;
(11) vimentin; and
(12) KIAK0002; each as set forth in Table 2;

comparing the expression levels of the at least ten genes to expression levels of the same set of genes from HCC samples obtained from human patients with recurrence of HCC and/or from HCC samples obtained from human patients without recurrence of HCC; and providing a likelihood of recurrence of HCC in the human subject on the basis of the comparison.

20. The system of claim 19, where the instructions include a formula for determining the likelihood of recurrence of HCC based on the expression levels of said genes indicative of recurrence of HCC, wherein the formula is $T(x)=0.053862\chi_1+0.038848\chi_2+0.030176\chi_3+0.001824\chi_4+0.096997\chi_5+0.017259\chi_6+0.015908\chi_7+0.103081\chi_8-0.093746\chi_9+0.024031\chi_{10}-0.005417\chi_{11}-0.119177\chi_{12}-11.046007$, wherein $\chi_1$ through $\chi_{12}$ are the normalized average differences of mRNAs expression levels for said genes (1) through (12), respectively, as listed in claim 19, wherein the likelihood of recurrence of HCC is determined by the T value, and wherein a positive T value indicates non-recurrence and a negative T value indicates recurrence of HCC.

* * * * *